United States Patent [19]

Ueno et al.

[11] Patent Number: 4,465,768
[45] Date of Patent: Aug. 14, 1984

[54] PATTERN-FORMATION METHOD WITH IODINE CONTAINING AZIDE AND OXYGEN PLASMA ETCHING OF SUBSTRATE

[75] Inventors: Takumi Ueno; Hiroshi Shiraishi, both of Hachioji; Takao Iwayanagi, Nerima; Takahiro Kohashi, Tsukui; Saburo Nonogaki, Meguro, all of Japan

[73] Assignee: Hitachi, Ltd., Tokyo, Japan

[21] Appl. No.: 397,903

[22] Filed: Jul. 13, 1982

[30] Foreign Application Priority Data

Jul. 15, 1981 [JP] Japan .................................. 56-109337
May 7, 1982 [JP] Japan .................................. 57-75231

[51] Int. Cl.$^3$ .......................... G03F 7/26; G03F 7/08; G03F 7/10; H01L 21/308
[52] U.S. Cl. ..................................... 430/296; 430/195; 430/197; 430/300; 430/302; 430/313; 430/317; 430/318; 430/323; 430/325; 430/329; 430/330; 430/309; 430/927; 430/967; 156/643

[58] Field of Search ............... 430/325, 323, 330, 302, 430/303, 300, 292, 294, 329, 309, 927, 195, 197, 296, 967, 313, 317, 318; 156/643

[56] References Cited

U.S. PATENT DOCUMENTS

| 3,748,135 | 7/1977 | Singh | 430/147 |
| 3,887,379 | 6/1975 | Clecak et al. | 430/927 |
| 3,923,522 | 12/1975 | Hata | 430/325 |
| 3,945,830 | 3/1976 | Yazawa et al. | 430/303 |
| 4,019,907 | 4/1977 | Tsunoda et al. | 430/325 |
| 4,388,397 | 6/1983 | Kanai | 430/325 |

Primary Examiner—Charles L. Bowers, Jr.
Attorney, Agent, or Firm—Antonelli, Terry & Wands

[57] ABSTRACT

A radiation-sensitive composition comprising an iodine-containing azide compound at least a part of which can be fixed substantially in a polymer by exposure to a radiation and a polymer, or a radiation-sensitive composition comprising an azide compound, an iodine compound at least a part of which can be fixed substantially in a polymer by exposure to a radiation and a polymer. This composition can be subjected to the dry development with oxygen plasma after the exposure followed by heating.

19 Claims, 3 Drawing Figures

PATTERN-FORMATION METHOD WITH IODINE CONTAINING AZIDE AND OXYGEN PLASMA ETCHING OF SUBSTRATE

BACKGROUND OF THE INVENTION

The present invention relates to a radiation-sensitive composition and pattern-formation method using the same.

In conventional pattern-formation methods, a coating film of a radiation-sensitive composition is exposed to a radiation of a given pattern and then the coating film is immersed in a liquid developer (mainly an organic solvent) or the liquid developer is sprayed over the surface of the coating film to form a pattern by wet development technique. However, this wet development technique has a defect that a negative-working composition used in a system employing a crosslinking reaction is swollen. This constitutes a serious obstacle to the formation of a fine pattern.

For overcoming this defect, there has been proposed a dry development technique wherein plasma is used for the development. If the dry development is effected until a region to be removed, i.e. an unexposed region, has completely been removed in the negative-working composition, the surface of an exposed region to be left is also etched to a considerable extent and the normalized film remaining (rate of thickness of remaining film to the initial film thickness) is reduced extremely. Thus, if this method is employed practically, many problems are posed.

SUMMARY OF THE INVENTION

An object of the present invention is to provide a radiation-sensitive composition suitable for the dry development and a pattern-formation method using the same.

The above and other objects of the present invention can be attained by using an iodine-containing azide compound at least a part of which can be fixed substantially in a polymer layer by exposure to a radiation and a polymer substantially having compatibility with said azide compound as well as by applying a pattern-forming method using them.

BRIEF DESCRIPTION OF THE DRAWINGS

FIGS. 1-3 illustrate the present invention.

DETAILED DESCRIPTION OF PREFERRED EMBODIMENTS

In the radiation-sensitive composition of the present invention, the iodine-containing azide compound may be replaced with an azide compound and an organic iodine compound at least a part of which can be fixed substantially in the polymer by exposure to a radiation. Namely, the composition is characterized by comprising an azide compound, an organic iodine compound at least a part of which can be fixed substantially in a polymer layer by expoosure to a radiation and a polymer substantially having compatibility with the azide compound and the iodine compound.

The pattern-formation method of the present invention is characterized by comprising the steps of forming a coating film of the radiation-sensitive composition, exposing the coating film to a radiation having a desired pattern, heating the coating film to remove the iodine-containing azide compound or iodine compound in an unexposed region and exposing the coating film to an oxygen-containing plasma to remove the unexposed part.

The term "radiation" herein refers to visible light, ultraviolet light, X-ray, electron beam and ion beam in a broad sense.

Though mechanisms of the reaction or decomposition of the azide compound caused by exposure to the radiation have not been elucidated yet, it may be said that at least an iodine-containing moiety of the compound is substantially fixed in the polymer layer. It is considered that by the presence of iodine, a nonvolatile, oxygen-containing, plasma-resistant substance is formed on the surface layer in the oxygen-containing plasma. This is a property peculiar to iodine compounds. Chlorine- or bromine-containing compounds are free of such a property.

A reason why an iodine-containing azide compound is substantially fixed in the polymer layer in the composition containing said compound is that said compound or a part thereof is directly linked with the polymer or, otherwise, converted into its dimer or polymer and, therefore, is not dissipated even when heated.

When the composition containing the iodine compound and azide compound is used, there may be considered two cases, i.e. (1) a case wherein the azide compound is directly linked with both iodine compound and polymer (particularly in case the azide compound is a diazide compound) and (2) a case wherein a part of the azide compound is linked with the iodine compound, whereby the iodine compound is not dissipated even when heated and the other part of the azide compound is linked with the polymer to alter its solubility. The term "azide compound" involves also a part of compounds formed by the photolysis and converted compounds. The mechanism described above is only an estimation and it does not exert any influence on the construction of the invention.

The heating temperature of the coating film should be one at which the iodine-containing azide compound or the iodine compound in the unexposed region is dissipated. In other words, it should be higher than a sublimation temperature or boiling point of said compound. The heating temperature is, therefore, variable depending on the variety of the iodine-containing azide compound or iodine compound used. If the coating film is placed under reduced pressure, the heating temperature can be lowered to some extent. The upper limit of the heating temperature should be below a decomposition point of the polymer.

The term "polymer substantially compatible with the azide compound or iodine compound" refers to a polymer capable of forming a coating film of a substantially homogeneous composition with them. Even if polymer $P_1$ is incompatible with the compound, a mixture of polymer $P_1$ with another polymer $P_2$ compatible with polymer $P_1$ may be used, if this mixture $(P_1+P_2)$ is compatible with said compound.

This polymer has preferably excellent film-forming characteristics.

As for the proportion of the polymer to the iodine-containing azide compound in the radiation-sensitive composition, it is preferred that the amount of the iodine-containing azide compound is 10-80 wt.%, particularly 30-60 wt.%, based on the composition.

Figure 1:
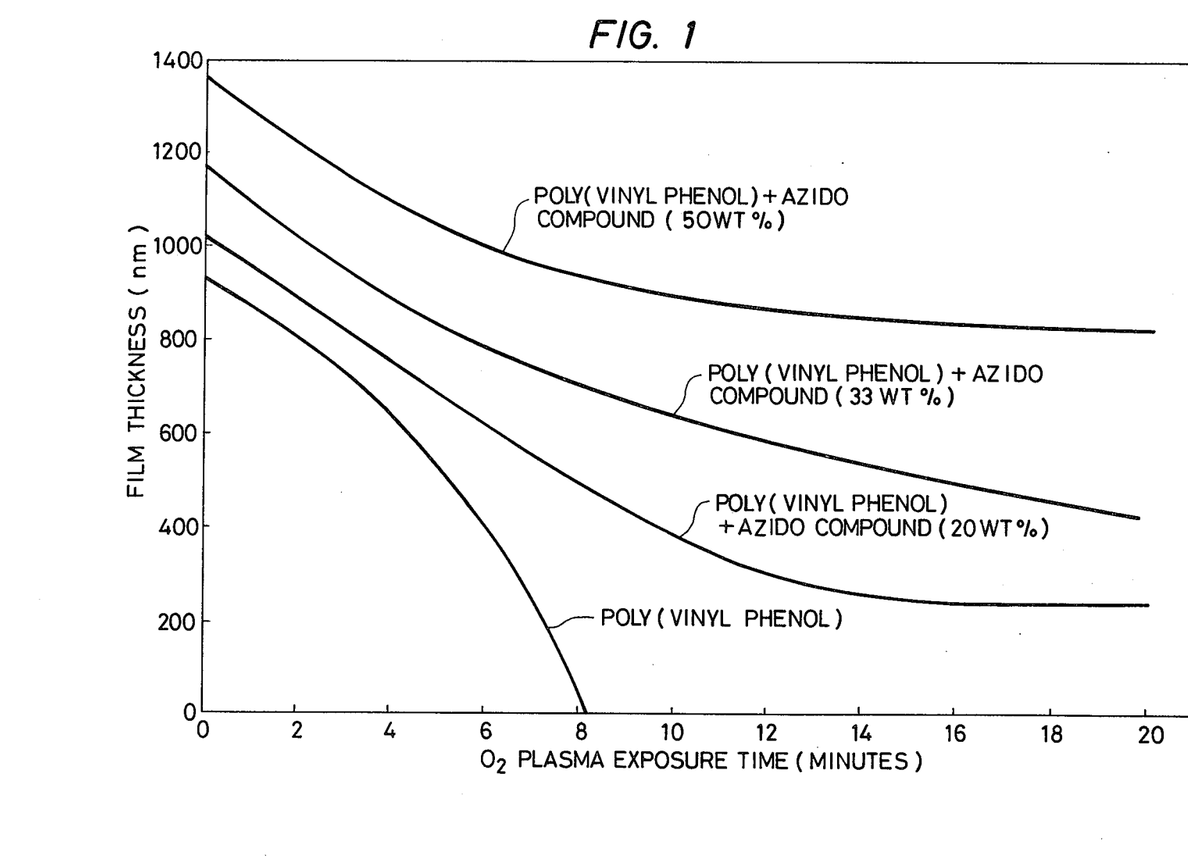

FIG. 1 shows changes in film thickness observed when films having various proportion of the polymer and the azide compound were exposed to oxygen plasma. Though it should be taken into consideration that the initial thicknesses were different from one another and about 50% of a coating film containing 20 wt.% of the azide compound (2,4,6-triiodophenyl-4'-azidobenzoate) remained even after exposure to oxygen plasma for about 8 min, while a coating film containing only the polymer (polyvinylphenol) disappeared after exposure to oxygen plasma for about 8 min. About 60% and 75% of coating films containing 33 wt.% and 50 wt.%, respectively, of the same azide compound remained after exposure to oxygen plasma for 8 min. This fact indicates that the normallized film remaining is increased as the amount of the iodine-containing azide compound is increased. However, it will be apparent from the above description that a certain amount of the polymer is necessary for fixing the azide compound. Therefore, an amount in the above-mentioned range is preferred. The plasma irradiation conditions are shown in Example 1 given below.

The proportion of the polymer, organic iodine compound and azide compound in the radiation-sensitive composition comprising these three compounds is preferably 1:0.1–3:0.05–2, particularly 1:0.4–2:0.1–1, by weight.

Experimental data of the resistance of the composition to oxygen plasma will be shown in Table 1, which shows relative removal rates of films by oxygen plasma measured after hardening of coating films comprising polystyrene, 3,3'-diaziododiphenyl sulfone and iodoform by light. It is apparent from Table 1 tha oxygen plasma resistance is increased remarkably as the amount of iodoform (iodine compound) is increased. It is understood, therefore, that the coating film can be used as an oxygen plasma-resisting mask. The experimental conditions were the same as in FIG. 1.

TABLE 1

| Polystyrene (part by wt.) | Diazide compound (part by wt.) | Iodoform (part by wt.) | Relative removal rate of film |
|---|---|---|---|
| 1 | 0.2 | 0 | 1.0 |
| 1 | 0.2 | 0.24 | 0.77 |
| 1 | 0.2 | 0.59 | 0.46 |
| 1 | 0.2 | 1.53 | 0.33 |

As the polymer, there may be used poly-N-vinylcarbazole, polyacenaphthylene, polyvinylidene fluoride, poly-N-vinylpyrrolidone, polyglycidyl methacrylate, polystyrene, polyalkyl methacrylates, cyclic polyisoprene, poly-4-methylstyrene, polymethacrylonitrile, poly-4-vinylpyridine, poly-4-bromostyrene, polyvinylbenzyl chloride, polybutadiene, poly-4-chlorostyrene, epoxidized polybutadiene, polyvinyl acetate, polyvinyl cinnamate, polyvinyl chloride, polychloroprene, polyvinyl bromide, polyepichlorohydrin, polyvinylphenol, polyvinyl alcohol, polyvinylidene chloride, polyacrylonitrile, poly-α-methylstyrene, polymethyl isopropenyl ketone, polyacrylamide, polyvinyl methyl ketone, polybutene-1 sulfone, polystyrene sulfone, polyisobutylene, a phenolic resin such as novolak resin, styrene-/maleic anhydride copolymer, cellulose acetate hydrogenphthalate, polyvinyl hydroxybenzoate, polyvinyl hydroxybenzal or acrylic resin. These polymers may be used also in the form of a copolymer. Further, ordinarily used polymers other than those mentioned above having film-forming properties and compatibility with said compounds may also be used. These polymers may be used either alone or in the form of a mixture of two or more of them.

As the polymers, those containing a benzene ring or rubbery polymers are preferred from the viewpoint of dry etching resistance of them.

When the pattern formation method of the present invention is carried out according to the dry development, the iodine-containing polymer cannot substantially be used as the polymer. A reason therefor is that even if the iodine-containing compound is removed from the unexposed region of the coating film by heating, the iodine-containing polymer remains in the film, whereby it exhibits a resistance to oxygen plasma. However, it will be understood from, for example, Table 1 given above that if the iodine content is low, a difference in the relative removal rate of film in this case from that of iodine-free film is insignificant. Since the iodine compound or iodine-containing azide compound is present in the exposed region, the total of iodine contained therein and that contained in the polymer is relatively large and the relative removal rate of the film is reduced. Thus, even if the polymer contains only a small amount of iodine, a pattern may be formed in the coating film according to the dry development.

As the azide compounds containing iodine, the compounds of the following general formula may be mentioned:

(I)

wherein $R_x$ and $R_y$ each represent an element or atomic group selected from the group consisting of hydrogen, alkyl group, nitro group, halogen, amino group, monoalkylamino group, acyl group, dialkylamino group, alkoxyl group, hydroxyl group, sulfonic acid group, sulfonic acid ester group, carboxylic acid group and carboxylic acid ester group.

As examples of these compounds, there may be mentioned p-azidoiodobenzene, 2,6-diiodo-4-nitroazidobenzene, 2-chloro-4-iodoazidobenzene, 2,6-dichloro-4-iodoazidobenzene, 2-bromo-4-iodoazidobenzene, 2,6-dibromo-4-iodoazidobenzene, 2-methyl-4-iodoazidobenzene and 2-methoxy-4-iodoazidobenzene.

Further, azide compounds of the following general formula may be mentioned:

(II)

wherein Y represents an atomic group selected from the group consisting of $CH_2$, COO, OOC, $SO_3$ and $O_3S$ and $R_i$ represents an element or atomic group selected from the group consisting of I, $CH_2I$ and $CH_2CH_2I$.

As examples of these compounds, there may be mentioned 2-iodoethyl-4-azidobenzoate, iodomethyl-4-azidobenzoate, 4-azidophenyl iodoacetate and 4-iodomethylazidobenzene.

In addition, azide compounds of the following general formula may be mentioned:

(III)

wherein X represents an element or atomic group selected from the group consisting of $S_2$, $CH_2$, O, S, $SO_2$, CO, COO, $SO_3$, CH=CH and CH=CHCO and $R_x$ and $R_y$ have the same meaning as described above.

As examples of these compounds, there may be mentioned 2,4,6-triiodophenyl-4'-azidobenzoate, 3-iodophenyl-4'-azidobenzoate, 4-azido-4'-iododiphenyl sulfide and 4-azido-4'-iodobenzophenone.

In the above-mentioned, iodine-containing azide compounds, those having one aromatic ring and those having the iodine atoms directly bonded with the benzene ring are preferred in view of easiness of dissipation by heat.

A combination of an azide compound containing a polar group such as carboxylic acid group with a polymer having a polar group such as polyvinylphenol is not preferred, since dissipation of the azide compound by heat becomes difficult.

As the iodine compounds used in the present invention, there may be mentioned diiodomethane, iodoform, iodoethane, 1-iodobutane, 1-iodoheptane, 1-iodopropane, 2-iodopropane, 1,2-diiodoethane, 1,4-diiodobutane, iodotrimethylsilane, 2-iodo-1,1,1-trifluoroethane, iodomethyltrimethylsilane, iodoacetamide, iodoacetic acid, 3-iodopropionic acid, 2-iodoethanol, 2-iodoaniline, 3-iodoaniline, 4-iodoaniline, 4-iodoanisole, 5-iodoanthranilic acid, o-iodobenzoic acid, m-iodobenzoic acid, p-iodobenzoic acid, p-iodobenzenesulfonyl chloride, o-iodobenzyl alcohol, m-iodobenzyl alcohol, p-iodobenzyl alcohol, iodobenzene, o-diiodobenzene, m-diiodobenzene, p-diiodobenzene, o-iodobenzyl chloride, 1-iodo-2-nitrobenzene, 1-iodo-3-nitrobenzene, 1-iodo-4-nitrobenzene, 2-iodophenol, 3-iodophenol, 4-iodophenol, 5-iodosalicylic acid, o-iodotoluene, m-iodotoluene, p-iodotoluene, o-iodo-$\alpha,\alpha,\alpha$-trifluorotoluene, 2-iodo-6-methyl-3-pyridinol, 2-iodo-3-pyridinol, 4-iodopyrazole, 2-iodothiophene, 3-iodothiophene, 2,6-diiodo-4-nitroaniline, 2,6-diiodo-4-nitrophenol, 3,5-diiodo-4-pyridone-N-acetate, 4-hydroxy-3,5-diiodobenzoic acid, 2,4,5-triiodobenzoic acid, 3,4,5-triiodobenzoic acid and 2,4,6-triiodophenol. They may be used either alone or in the form of a mixture of two or more compounds. These iodine compounds are free of azido group.

As the azide compounds, there may be mentioned those of the general formula:

(IV)

wherein A represents an element or a substituent selected from the group consisting of O, S, $CH_2$, $CH_2CH_2$, $SO_2$, $S_2$, CO, COO, $SO_3$, CH=CH and CH=CHCO, and X, Y and Z each represent an element or a substituent selected from the group consisting of an azido group, hydrogen, alkyl group, nitro group, halogen, amino group, monoalkylamino group, alkoxyl group, hydroxyl group, sulfonic acid group, sulfonic acid ester group, carboxylic acid group and carboxylic acid ester group, and those of the general formula:

(V)

wherein X, Y and Z have the same meaning as above.

Organic azide compounds other than those shown above may also be used. The azide compounds may be used either alone or in the form of a mixture of them.

Some of the compounds wherein at least one of X, Y and Z represents iodine are the same as the above-mentioned iodine-containing azide compounds. These iodine-containing azide compounds may also be used in combination with the iodine compound, if they are removable from the coating film in an unexposed region by heating.

As concrete examples of the azide compounds of general formula (IV), there may be mentioned 4,4'-diazidodiphenyl ether, 4,4'-diazidodiphenyl sulfide, 4,4'-diazidodiphenyl sulfone, 3,3'-diazidodiphenyl sulfone, 4,4'-diazidodiphenylmethane, 3,3'-dichloro-4,4'-diazidodiphenylmethane, 4,4'-diazidodiphenyl disulfide, 4,4'-diazidobibenzyl, 2,4,6-triiodophenyl-4'-azidobenzoate, 3-iodophenyl-4'-azidobenzoate, 4-azido-4'-iododiphenyl sulfide and 4-azido-4'-iodobenzophenone.

As concrete examples of the azide compounds of general formula (V), there may be mentioend p-azidoiodobenzene, 2,6-diiodo-4-nitroazidobenzene, 2-chloro-4-iodoazidobenzene, 2,6-dichloro-4-iodoazidobenzene, 2-bromo-4-iodoazidobenzene, 2,6-dibromo-4-iodoazidobenzene, 2-methyl-4-iodoazidobenzene and 2-methoxy-4-iodoazidobenzene.

As other azide compounds, there may be mentioned, for example, 2-iodomethyl-4-azidobenzoate.

It is preferred to use the diazide compounds as the azide compounds, since they fix the iodine compounds firmly.

Also in the radiation-sensitive composition comprising the iodine compound, azide compound and polymer wherein the iodine compound contains a polar group such as carboxylic acid group or wherein the azide compound contains iodine and a polar group such as carboxylic acid group, it is not preferred to use a polar group-containing polymer such as polyvinylphenol, novolak resin, styrene/maleic anhydride copolymer, cellulose acetate hydrogenphthalate, polyvinyl hydroxybenzoate, polyvinylhydroxybenzal, polymethacrylic acid or polyacrylic acid, because these compounds are difficultly dissipated by heating in the dry development.

The sensitive composition of the present invention can be used also in an ordinary wet development technique. In this case, it is preferred that the azide compound is a diazide compound or that when the azide compound is a monoazide compound, a polymer having a polar group such as polyacrylic acid, particularly, a polymer soluble in an aqueous alkali solution is used.

When other compositions wherein the azide compound is a monoazide compound and the polymer contains no polar group are used, it is not preferred to employ the wet development technique.

As the polymers soluble in an aqueous alkali solution, there may be mentioned, for example, polyvinylphenol, novolak resin, styrene/maleic anhydride copolymer, cellulose acetate hydrogenphthalate, polyvinyl hydroxybenzoate, polyvinylhydroxybenzal, polymethacrylic acid and polyacrylic acid.

In case the wet development technique is employed, an unexposed part is removed with a solvent by an ordinary method after exposure to the radiation.

The radiation-sensitive composition of the present invention has an excellent resistance to oxygen plasma as described above and, therefore, it may be used for the production of a printing plate. In this technique, for example, a coating film of the composition of the present invention is formed on a nylon base, a desired pattern is formed and the base is etched using oxygen plasma. Accordingly, the reduction of resolution due to the swelling of the base with a solvent can be prevented.

Any oxygen-containing plasma may be used, though it is preferred to use oxygen plasma per se.

The following examples will further illustrate the present invention. First, processes for synthesizing the iodine-containing azide compounds will be described.

p-Azidoiodobenzene:

6 g of p-iodoaniline was dispersed in a solution comprising 25 cc of water and 7.5 cc of 36% hydrochloric acid and cooled with ice. 2.1 g of sodium nitrite was dissolved in 13 ml of water and the resulting solution was added dropwise slowly to the dispersion to effect the diazotization reaction. A solution of 2.5 g of sodium azide in 18 ml of water was added dropwise thereto and, after stirring for one hour, the mixture was subjected to extraction with benzene. After the dehydration with sodium sulfate, benzene was evaporated to obtain p-azidoiodobenzene.

$\lambda_{max}$: 260 nm, m.p. 33° C.

2,6-Diiodo-4-nitroazidobenzene:

5 g of 2,6-diiodo-4-nitroaniline was dissolved in 20 ml of conc. sulfuric acid and cooled with ice. Sodium nitrite previously vacuum-dried was added to the solution in portions to effect the diazotization reaction at 0°–5° C. The reaction product was added dropwise to ice-water to dilute the sulfuric acid. A solution of 1.4 g of sodium azide in 10 cc of water was added dropwise to the mixture, stirred for about one hour, filtered and washed with water. After the recrystallization from ethanol followed by drying, 2,6-diiodo-4-nitroazidobenzene was obtained.

$\lambda_{max}$: 302 nm, m.p. 82° C.

2,4,6-Triiodophenyl-4'-azidobenzoate:

13.7 g of p-aminobenzoic acid was dispersed in a solution of 100 cc of water and 30 cc of 30% hydrochloric acid in an ordinary manner and the dispersion was cooled with ice. A solution of 8.3 g of sodium nitrite in 50 cc of water was added dropwise to the dispersion to effect the diazotization reaction. A solution of 10.1 g of sodium azide in 70 cc of water was added dropwise to the mixture, stirred for about one hour, filtered and vacuum-dried to obtain p-azidobenzoic acid. 5.4 g of the thus obtained p-azidobenzoic acid was dissolved in 10 cc of dimethylformamide and 25 g of thionyl chloride was added dropwise to the solution. The mixture was stirred for about one hour and the product was added dropwise to ice-water. After filtration followed by washing with water and vacuum drying, p-azidobenzoyl chloride was obtained.

0.9 g of p-azidobenzoyl chloride and 2.4 g of 2,4,6-triiodophenol were dissolved in 60 cc of dioxane. The resulting solution was mixed with a solution of 0.2 g of sodium hydroxide in 20 ml of water and the mixture was left to stand overnight and then poured into water. A solid matter thus formed was filtered out, washed with water and dried under vacuum to obtain 2,4,6-triiodophenyl-4'-azidobenzoate.

$\lambda_{max}$: 278 nm, m.p. 115° C.

3-Iodophenyl-4'-azidobenzoate:

3-Iodophenyl 4-azidobenzoate was obtained by reacting azidobenzoyl chloride obtained as above with m-iodophenol in the same manner as above.

$\lambda_{max}$: 278 nm.

EXAMPLE 1

Polystyrene having a weight-average molecular weight (Mw) of about 270,000 was dissolved in chlorobenzene to obtain a 7 wt.% solution. Then, p-azidoiodobenzene was added to the solution to obtain a resist solution. The mixing ratio of polystyrene to p-azidoiodobenzene was 1:0.6, by weight. The resist solution was applied to the surface of a silicon wafer by means of a spinner to form a film having a thickness of 0.6 $\mu$m. After exposing the film to a light of a Xe-Hg lamp via a test pattern mask for 20 sec, it was post-baked at 100° C. for 30 min to obtain a sample for the plasma development. The development was effected as shown below by means of an experimental apparatus consisting of a parallel-plate plasma reactor having a maximum output of 600 W and an electrode diameter of 60 mm. The sample was placed on a lower electrode and, after degassing, oxygen gas was introduced therein to control pressure in the reactor to 0.5 Torr. A high frequency power of 13.56 MHz was applied thereto and oxygen plasma was formed in the plasma reactor at an output of 55 W for 6 min. After degassing in the reactor, the pressure was returned to atmospheric pressure. The sample was taken out and subjected to the microscopic examination to reveal that, unlike a product of the wet development method, the product thus obtained had a repetition pattern of lines having a width of 1 $\mu$m not swollen at all and arranged at intervals of 1 $\mu$m with high accuracy.

EXAMPLE 2 p-Azidoiodobenzene was added to a 10 wt.% solution of cyclic polyisoprene in xylene to obtain a resist solution. The mixing ratio of cyclic polyisoprene to p-azidoiodobenzene was 1:1, by weight. The resist solution was applied to the surface of a silicon wafer by means of a spinner to form a film having a thickness of about 0.9 $\mu$m. After exposing the film to a light of a Xe—Hg lamp, it was post-baked at 100° C. for 30 min to obtain a sample for the plasma development. After effecting the development in the same manner as in Example 1, the product was subjected to the microscopic examination to reveal that, unlike a product of the wet development method, the product thus obtained had the same, minute pattern as in Example 1.

Figure 2:
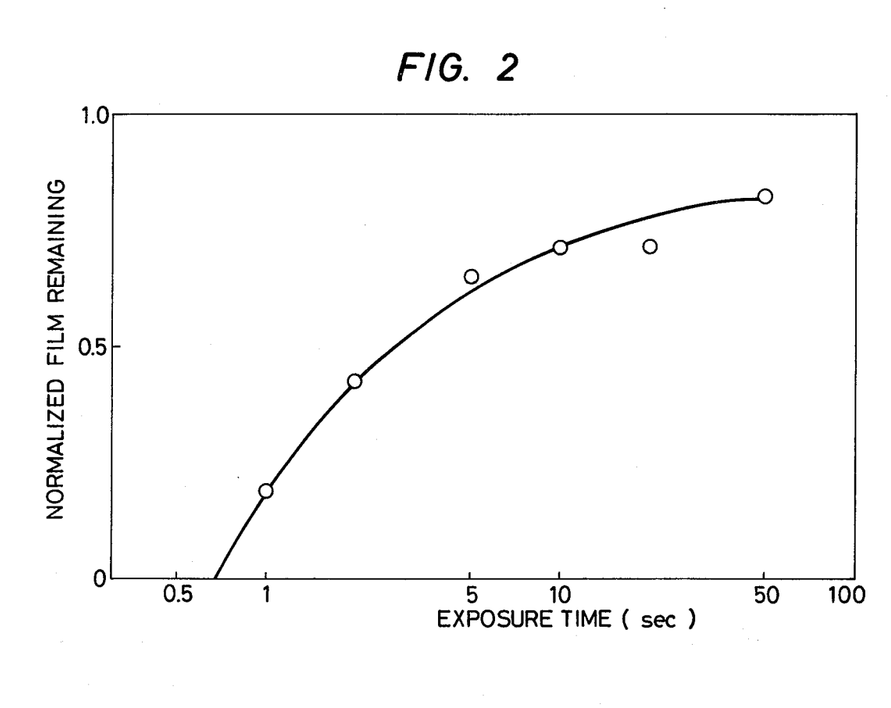

A relationship between the exposure time and normalized film remaining is shown in FIG. 2. After the exposure for longer than about 3 sec, the normalized film remaining was higher than 50%.

EXAMPLE 3 p-Azidoiodobenzene was added to a 6 wt.% solution of polymethyl methacrylate having a weight-average molecular weight (Mw) of about 600,000 in ethyl cellosolve acetate to obtain a resist solution. The mixing ratio of polymethyl methacrylate to p-azidoiodobenzene was 1:1, by weight. The resist solution was applied to the surface of a silicon wafer by means of a spinner to form a film having a thickness of about 0.5 $\mu$m. After exposing the film to a light of a Xe-Hg lamp via a test pattern mask for 20 sec, it was post-baked at 100° C. for 30 min to obtain a sample for the plasma development. After effecting the development with oxygen plasma in the same manner as in Example 1, the product was subjected to the microscopic examination to reveal that, unlike a product of the wet development method, the product thus obtained had a repetition pattern of lines having a width of 1 $\mu$m not swollen at all and arranged at intervals of 1 $\mu$m with high accuracy.

EXAMPLE 4

A resist solution having the same composition as in Example 1 having a mixing ratio of polystyrene to p-azidoiodobenzene of 1:1, by weight, was used. The resist solution was applied to the surface of a silicon wafer in the same manner as in Example 1. After the exposure followed by the post-baking, the development was effected with oxygen plasma. The normalized film remaining was superior to that obtained in Example 1. The sample was subjected to the microscopic examination to reveal that, unlike a product of the wet development method, the product thus obtained had a repetition pattern of lines having a width of 1 $\mu$m not swollen at all and arranged at intervals of 1 $\mu$m with high accuracy.

EXAMPLE 5

2,4,6-Triiodophenyl-4'-azidobenzoate was added to a 20% solution of polyvinylphenol having a weight-average molecular weight (Mw) of about 3000 in methyl cellosolve acetate to obtain a resist solution. The mixing ratio of polyvinylphenol to the azide compound was 1:1, by weight. The resist solution was applied to the surface of a silicon wafer by means of a spinner to form a film having a thickness of about 0.9 $\mu$m. After exposing the film to a light of a Xe-Hg lamp via a test pattern mask for 20 sec, it was post-baked at 140° C. for 60 min to obtain a sample for the plasma development. After effecting the development with oxygen plasma in the same manner as in Example 1, the product was subjected to the microscopic examination to reveal that, unlike a product of the wet development method, the product thus obtained had a repetition pattern of lines having a width of 1 $\mu$m not swollen at all and arranged at intervals of 1 $\mu$m with high accuracy.

EXAMPLE 6

2,6-Diiodo-4-nitroazidobenzene was added to a 20 wt.% solution of polyvinylphenol having a weight-average molecular weight (Mw) of about 3000 in methyl cellosolve acetate to obtain a resist solution. The mixing ratio of polyvinylphenol to the azide compound was 1:0.5, by weight. The resist solution was applied to the surface of a silicon wafer by means of a spinner to form a film having a thickness of about 0.9 $\mu$m. After exposing the film to a light of a Xe-Hg lamp via a test pattern mask for 20 sec, it was post-baked at 140° C. for 60 min to obtain a sample for the plasma development. After effecting the development with oxygen plasma in the same manner as in Example 1, the product was subjected to the microscopic examination to reveal that, unlike a product of the wet development method, the product thus obtained had a repetition pattern of lines having a width of 1 $\mu$m not swollen at all and arranged at intervals of 1 $\mu$m with high accuracy.

EXAMPLE 7

Polyvinylphenol having a weight-average molecular weight (Mw) of about 5800 was dissolved in methyl cellosolve acetate to obtain a 20 wt.% solution. Then, 3,3'-diazidodiphenyl sulfone and 2,4,6-triiodophenol were added to the solution to obtain a resist solution. The mixing ratio of polyvinylphenol:3,3'-diazidodiphenyl sulfone:2,4,6-triiodophenol was 1:0.2:0.7, by weight. The resist solution was applied to the surface of a silicon wafer by means of a spinner to form a film having a thickness of about 0.85 $\mu$m. After exposing the film to a light of a Xe-Hg lamp via a test pattern mask for 20 sec, it was post-baked at 140° C. for 60 min to obtain a sample for the plasma development. This sample was placed in the same plasma-forming apparatus as in Example 1 and oxygen plasma was formed for 8 min. After degassing in the reactor, the pressure was returned to atmospheric pressure. The sample was taken out and subjected to the microscopic examination to reveal that the product had a repetition pattern of lines having a width of 1 $\mu$m not swollen at all and arranged at intervals of 1 $\mu$m with high accuracy.

EXAMPLE 8

Figure 3:
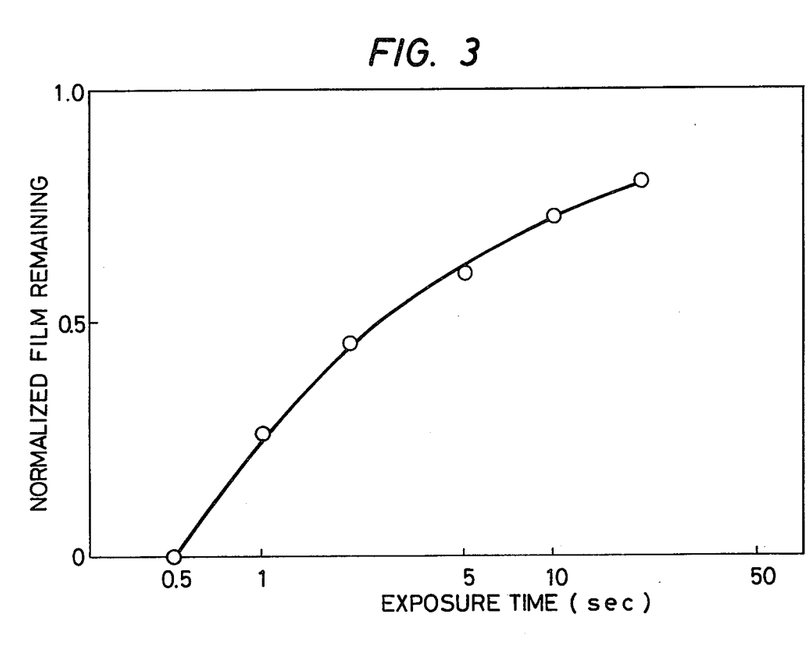

A result solution having the same composition as in Example 7 except that the mixing ratio of polyvinylphenol:3,3'-diazidodiphenyl sulfone:2,4,6-triiododphenol was altered to 1:0.2:1, by weight. The resist solution was applied to a silicon wafer in the same manner as in Example 7. After the exposure followed by the post-baking, it was subject to the development with oxygen plasma in the same manner as in Example 7. The exposure time and normalized film remaining were as shown in FIG. 3. The film was superior to that of Example 7 with respect to the normalized film remaining. The product was subjected to the microscopic examination to reveal that it had a repetition pattern of lines having a width of 1 $\mu$m not swollen at all and arranged at intervals of 1 $\mu$m with high accuracy.

EXAMPLE 9

Polystyrene having a weight-average molecular weight (Mw) of about 270,000 was dissolved in chlorobenzene to obtain a 7 wt.% solution. Then, 3,3'-diazidodiphenyl sulfone and m-iodophenol were added to the solution to obtain a resist solution. The mixing ratio of polystyrene:3,3'-diazidodiphenyl sulfone:m-iodophenol was 1:0.2:0.5, by weight. The resist solution was applied to the surface of a silicon wafer by means of a spinner to form a film having a thickness of about 0.76 $\mu$m. After exposing the film to a light of a Xe-Hg lamp, it was post-baked at 110° C. for 85 min to obtain a sample for the plasma development. After effecting the development with oxygen plasma in the same manner as in Example 7, the product was subjected to the microscopic examination to reveal that, unlike a product of the wet development method, the product thus obtained had the same, fine pattern as in Example 7.

EXAMPLE 10

Polystyrene having a weight-average molecular weight (Mw) of about 270,000 was dissolved in chlorobenzene to obtain a 7 wt.% solution. Then, 3,3'- diazidodiphenyl sulfone and m-diiodobenzene were added to the solution to obtain a resist solution. The mixing ratio of polystyrene:3,3'-diazidodiphenyl sulfone:m-diiodobenzene was 1:0.2:0.5, by weight. The resist solution was applied to the surface of a silicon wafer by means of a spinner to form a film having a thickness of 0.86 μm. After exposing the film to a light of a Xe-Hg lamp, it was post-baked at 110° C. for 60 min to obtain a sample for the plasma development. After effecting the development with oxygen plasma in the same manner as in Example 7, the product was subjected to the microscopic examination to reveal that, unlike a product of the wet development method, the product thus obtained had the same, fine pattern as in Example 7.

EXAMPLE 11

Polystyrene having a weight-average molecular weight (Mw) of about 270,000 was dissolved in chlorobenzene to obtain a 7 wt.% solution. Then, 3,3'-diazidodiphenyl sulfone and iodoform were added to the solution to obtain a resist solution. The mixing ratio of polystyrene:3,3'-diazidodiphenyl sulfone:iodoform was 1:0.2:0.5, by weight. The resist solution was applied to the surface of a silicon wafer by means of a spinner to form a film having a thickness of 0.86 μm. After exposing the film to a light of a Xe-Hg lamp, it was postbaked at 110° C. for 90 min to obtain a sample for the plasma development. After effecting the development with oxygen plasma in the same manner as in Example 1, the product was subjected to the microscopic examination to reveal that, unlike a product of the wet development method, the product thus obtained had the same, fine pattern as in Example 7 and was free of swelling.

When the iodine compound or azido compounds used in above Examples 7–11 were replaced with other iodine compounds or azido compounds, a fine pattern could also be obtained by the dry development.

EXAMPLE 12

13 parts by weight of 2,4,6-triiodophenol was added to 100 parts by weight of a solution comprising 20 parts by weight of poly-p-vinylphenol, 4 parts by weight of 3,3'-diazidodiphenyl sulfone and 80 parts by weight of cyclohexanone to obtain a resist solution. The resist solution was applied to the surface of a silicon wafer by means of a spinner and baked at 80° C. for 20 min in air to obtain a resist film having a thickness of 1.1 μm which was used as an exposure sample. After exposing the sample to a light of a 600 W Xe-Hg lamp via a test pattern mask for 5 sec, it was immersed in a 0.95 wt.% aqueous solution of tetramethylammonium hydroxide used as a developer for 30 sec to effect the development of the resist film. The product was subjected to the microscopic examination to reveal that the product thus obtained had a repetition pattern of lines having a width of 1 μm not swollen at all and arranged at intervals of 1 μm with high accuracy.

EXAMPLE 13

20 parts by weight of m,p-cresol novolak resin, 6 parts by weight of 4-azido-4'-methoxychalcone and 10 parts by weight of 2,4,6-triiodophenol were dissolved in 80 parts by weight of methyl cellosolve acetate to obtain a resist solution. The resist solution was applied to the surface of a silicon wafer and baked at 80° C. for 20 min to obtain a resist film having a thickness of 0.9 μm.

After exposing the film to a light of a 500 W ultra-high pressure Hg lamp via a test pattern mask for 2 sec, it was developed with an aqueous solution of tetramethylammonium hydroxide to form a repetition pattern of lines having a width of 1 μm arranged at intervals of 1 μm with high accuracy.

The films were exposed to light in the above examples. Substantially the similar effects were obtained also when visible light, X-ray, electron beam or ion beam was used.

What is claimed is:

1. A method of forming a pattern characterized by comprising the steps of forming a coating film of a radiation-sensitive composition comprising an iodine-containing azide compound at least a part of which can be fixed substantially in a polymer layer by exposure to a radiation and a polymer substantially having compatibility with the azide compound, exposing the coating film to a radiation having a desired pattern, heating the coating film to remove the azide compound from an unexposed region of the coating film and exposing the coating film to an oxygen-containing plasma to remove the unexposed part.

2. A method of forming a pattern according to claim 1 wherein the amount of the azide compound is in the range of 10–80 wt.% based on the composition.

3. A method of forming a pattern according to claim 1 wherein a heating temperature of the coating film is above a sublimation temperature or boiling point of the azide compound.

4. A method of forming a pattern according to claim 1 wherein the radiation is U.V. light.

5. A method of forming a pattern according to claim 1 wherein the radiation is electron beams.

6. A method of forming a pattern according to claim 1 wherein the radiation is X-rays.

7. A method of forming a pattern according to claim 1 wherein the radiation is ion beams.

8. A method of forming a pattern according to anyone of claims 1–7 wherein the azide compound is at least one compound selected from the group consisting of azide compounds of the general formula:

wherein $R_x$ and $R_y$ each represent an element or atomic group selected from the group consisting of hydrogen, alkyl group, nitro group, halogen, amino group, monoalkylamino group, acyl group, dialkylamino group, alkoxyl group, hydroxyl group, sulfonic acid group, sulfonic acid ester group, carboxylic acid group or carboxylic acid ester group, azide compounds of the general formula:

wherein Y represents an atomic group selected from the group consisting of $CH_2$, COO, OOC, $SO_3$ and $O_3S$, and $R_i$ represents an element or atomic group selected from the group consisting of I, $CH_2I$ and $CH_2CH_2I$, and azide compounds of the general formula:

wherein X represents an element or atomic group selected from the group consisting of $S_2$, $CH_2$, O, S, $SO_2$, CO, COO, $SO_3$, CH=CH and CH=CHCO and $R_x$ and $R_y$ have the same meaning as described above.

9. A method of forming a pattern according to claim 8 wherein the azide compound is at least one compound selected from the group consisting of p-azidoiodobenzene, 2,6-diiodo-4-nitroazidobenzene, 2-chloro-4-iodoazidobenzene, 2,6-dichloro-4-iodoazidobenzene, 2-bromo-4-iodoazidobenzene, 2,6-dibromo-4-iodoazidobenzene, 2-methyl-4-iodoazidobenzene, 2-methoxy-4-iodoazidobenzene, 2-iodoethyl-4-azidobenzoate, iodomethyl-4-azidobenzoate, 4-azidophenyl iodoacetate, 4-iodomethylazidobenzene, 2,4,6-triiodophenyl-4'-azidobenzoate, 3-iodophenyl-4'-azidobenzoate, 4-azido-4'-iododiphenyl sulfide and 4-azido-4'-iodobenzophenone.

10. A method of forming a pattern characterized by comprising the steps of forming a coating film of a radiation-sensitive composition comprising an azide compound, an iodine compound at least a part of which can be fixed substantially in a polymer layer by exposure to a radiation and a polymer substantially having compatibility with the azide compound and the iodine compound, exposing the coating film to a radiation having a desired pattern, heating the coating film to remove the iodine compound from the unexposed region of the coating film and exposing the coating film to an oxygen-containing plasma to remove the unexposed part.

11. A method of forming a pattern according to claim 10 wherein the weight ratio of the polymer:iodine compound:azide compound is in the range of 1:0.1–3:0.05–2.

12. A method of forming a pattern according to claim 10 or 11 wherein a heating temperature of the coating film is above a sublimation temperature or boiling point of the iodine compound.

13. A method of forming a pattern according to claim 10 or 11 wherein the radiation is U.V. light.

14. A method of forming a pattern characterized by comprising the steps of forming a coating film of a radiation-sensitive composition comprising an azide compound, an iodine compound at least a part of which can be fixed substantially in a polymer by exposure to a radiation and a polymer substantially having compatibility with the azide compound and the iodine compound and soluble in an aqueous alkaline solution on a base, exposing the coating film to a radiation having a desired pattern, subjecting the coating film to the development with the aqueous alkaline solution to remove the unexposed part, and exposing the coating film and the base to an oxygen-containing plasma to etch the base.

15. A method of forming a pattern according to claim 14 wherein the polymer soluble in an aqueous alkaline solution is at least one polymer selected from the group consisting of polyvinylphenol, novolak resin, styrene/maleic anhydride copolymer, cellulose acetate hydrogenphthalate, polyvinyl hydroxybenzoate, polyvinylhydroxybenzal, polymethacrylic acid and polyacrylic acid.

16. A method of forming a pattern characterized by comprising the steps of forming a coating film of a radiation-sensitive composition comprising an iodine-containing azide compound at least a part of which can be fixed substantially in a polymer by exposure to a radiation and a polymer substantially having compatibility with the azide compound and soluble in an aqueous alkaline solution on a base, exposing the coating film to a radiation having a desired pattern, subjecting the coating film to the development with the aqueous alkaline solution to remove the unexposed part, and exposing the coating film and the base to an oxygen-containing plasma to etch the base.

17. A method of forming a pattern according to claim 16 wherein the polymer soluble in an aqueous alkaline solution is at least one polymer selected from the group consisting of polyvinylphenol, novolak resin, styrene/maleic anhydride copolymer, cellulose acetate hydrogen-phthalate, polyvinyl hydroxybenzoate, polyvinylhydroxybenzal, polymethacrylic acid and polyacrylic acid.

18. A method of forming a pattern according to claim 17, wherein the azide compound is at least one compound selected from the group consisting of p-azidoiodobenzene, 2,6-diiodo-4-nitroazidobenzene, 2-chloro-4-iodoazidobenzene, 2,6-dichloro-4-iodoazidobenzene, 2-bromo-4-iodoazidobenzene, 2,6-dibromo-4-iodoazidobenzene, 2-methyl-4-iodoazidobenzene, 2-methoxy-4-iodoazidobenzene, 2-iodoethyl-4-azidobenzoate, iodomethyl-4-azidobenzoate, 4-azidophenyl iodoacetate, 4-iodomethyl-azidobenzene, 2,4,6-triiodophenyl-4'-azidobenzoate, 3-iodophenyl-4'-azidobenzoate, 4-azido-4'-iododiphenyl sulfide and 4-azido-4'-iodobenzophenone.

19. A method of forming a pattern according to any one of claims 1–7 wherein the plasma is oxygen plasma.

* * * * *